United States Patent [19]

Hinshaw

[11] Patent Number: 4,804,424
[45] Date of Patent: Feb. 14, 1989

[54] NITRATE ESTER-MISCIBLE POLYETHER POLYMERS

[75] Inventor: Jerald C. Hinshaw, Logan, Utah

[73] Assignee: Morton Thiokol, Inc., Chicago, Ill.

[21] Appl. No.: 205,022

[22] Filed: Jun. 3, 1988

Related U.S. Application Data

[62] Division of Ser. No. 925,657, Oct. 19, 1986, abandoned.

[51] Int. Cl.$^4$ .............................................. C06B 45/10
[52] U.S. Cl. .................................. 149/19.6; 149/19.4; 528/362; 528/417
[58] Field of Search ............................ 149/19.4, 19.6; 528/362, 417

[56] References Cited

U.S. PATENT DOCUMENTS

| | | | |
|---|---|---|---|
| 3,925,505 | 12/1975 | Sextro I, et al. | 525/472 |
| 4,234,364 | 11/1980 | Robinson | 149/19.4 |
| 4,393,199 | 7/1983 | Manser | 528/408 |
| 4,405,762 | 9/1983 | Earl et al. | 149/194 |
| 4,483,978 | 11/1984 | Manser | 528/408 |
| 4,707,540 | 11/1987 | Manser et al. | 528/362 |
| 4,764,586 | 8/1988 | Manser et al. | 149/194 |

FOREIGN PATENT DOCUMENTS 1570628 10/1973 German Democratic Rep. .
758450 10/1956 United Kingdom ................ 528/417

OTHER PUBLICATIONS

Sextro et al (II), *Chem. Abs.*, 79 (#4), abs. #19644r (1973).
Noelken (II), *Chem. Abs.*, 80, abs. #134044c (1974).
Miyamura, *Chem. Abs.*, 90, abs. #64,498j (1979).
F. Govaert et al. *Chem. Abst.* 50 4108i (1956).

*Primary Examiner*—Edward A. Miller
*Attorney, Agent, or Firm*—Wayne E. Nacker; Gerald K. White

[57] ABSTRACT

Polyethers are formed by polymerizing oxetanes having one or two pendant groups which contain cyano moieties, particularly 3-cyanomethyl-3-methyl oxetane and 3,3-Bis(cyanomethyl) oxetane. The polyethers may also contain mer units derived from other cyclic ethers, including other oxetanes and tetrahydrofurans. The cyano group gives the polyether improved compatibility with nitrate ester plasticizers. The polyethers are curable with polyfunctional isocyanates to form binders for propellants, explosives or the like.

8 Claims, No Drawings

NITRATE ESTER-MISCIBLE POLYETHER POLYMERS

The Government has rights in this invention pursuant to Contract No. F04611-82-C-0065 awarded by the U.S. Air Force.

This invention relates generally to polyethers containing repeating mer units derived from cylic oxides. The polyethers are useful in formulating binders and binder compositions for explosives, propellants, gasifiers and the like. In particular, the invention relates to polyethers having improved miscibility with nitrate esters plasticizers which are commonly used in explosives, propellants and gasifiers.

This is a divisional of co-pending application Ser. No. 925,657, filed on Oct. 29, 1986, now abandoned.

BACKGROUND OF THE INVENTION

Solid propellants for rocket motors, solid explosives or the like contain energetic solids, including fuel particulates and oxidizer particulates, distributed throughout a polymeric binder. Among binders in common use in high energy formulations are those formulated from polyethylene glycol (PEG), polycaprolactone (PCP), and PEG/PCP mixtures. These binders are commonly plasticized with nitrate esters, such as nitroglycerine (NG), which enhance elastomeric properties of the polymers and further contribute substantially to the energy of the binders and the propellant or explosive compositions as a whole. Because the polymeric binders themselves have relatively low energies, efforts are continually made to develop more energetic binders.

It has been proposed to prepare binders by polymerizing cyclic ethers having from 2 to 4 carbon atoms in the ring plus energetic pendant groups and then curing the polyethers, for example, with isocyanates and crosslinking agents. Examples of such polyethers and methods of preparing the same are described in U.S. Pat. No. 4,483,978, the teachings of which are incorporated herein by reference. The '978 patent is specifically directed to polyethers having pendant nitro, nitrate and azido groups.

A continuing problem with polyether-based binders has been compatibility with nitrate ester plasticizers. In order to have sufficient energy for many propellant or explosive applications, the binders must stably immobilize substantial amounts of high-energy nitrate ester plasticizers, the desired weight ratio of plasticizer to polymer typically being at least about 2.0:1 and commonly at least about 2.5:1. If the binder is insufficiently miscible with nitrate ester plasticizers, the plasticizers will weep or exude from the binder.

SUMMARY OF THE INVENTION

In accordance with the present invention, polyethers are prepared having improved miscibility with nitroesters. The polyethers contain at least 20 molar percent and up to 100% of mer units derived from an oxetane or oxetanes, each having either one or two pendant groups including highly polar cyano moieties which enhance the miscibility of the polyethers with nitrate ester plasticizers. The polyethers are curable using polyfunctional isocyanates to form elastomeric binders, and the cured binders likewise exhibit good compatibility with nitrate esters. In addition, binders formed from the polyethers exhibit improvement in propellant low-temperature strain and stress tolerability.

DETAILED DESCRIPTION OF THE PREFERRED EMBODIMENTS

In accordance with the present invention, novel polyethers are provided which contain cyano moieties in pendant groups and which exhibit improved compatibility with nitrate ester plasticizers, such as are commonly used in propellants, explosive and gasifier systems. The polyethers exhibit good functionality and are curable with isocyanates to form elastomeric binders. Compositions of at least two parts by weight nitroester plasticizer to one part by weight binder are stabilized by the cyano groups.

The novel polyethers in accordance with the inventions contain subunits derived from oxetanes having the general formula:

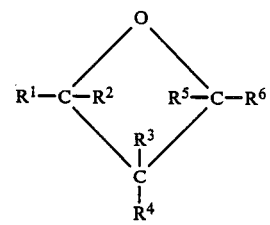

wherein at least four of $R^1$-$R^6$ are —H and at least one of $R^1$-$R^6$ has the formula $-(CH_2)_n-CN$, where n is at least 1. The remaining one of $R^1$-$R^6$ may likewise have the formula $-(CH_2)_n-CN$, where n is at least 1, or it may be selected from a variety of pendant groups, such as are known in the art of oxetane monomers, having functional moieties including but not limited to alkyl, nitrate, nitro, azido, alcohol, ester and ether groups. When polymerized, the resulting polyether contains mer units having the formula:

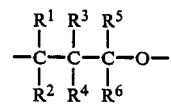

wherein $R^1$-$R^6$ are defined above.

Polyethers in accordance with the invention may be homopolymers of cyano moiety-containing oxetanes as defined above but may also be copolymers containing up to about 80 molar percent of one or more monomers derived from cyclic ethers having the general formula:

wherein $C_p$ represents saturated ring carbons and p is between 2 and 4. That is, polyethers in accordance with the present invention contain between about 20 and 100 molar percent of cyano-containing mers as described above. The cyclic ethers which may be copolymerized with the cyano-containing oxetanes include other oxetanes (p=3); ethylene oxide (p=2) and tetrahydrofuran and its derivatives (p=4). The comonomer may contain a variety of pendant groups tailored to the requirements of the binder polymer, having functional moieties including but not limited to cyano, alkyl, nitrate, nitro, azido, alcohol, ether and ester groups. The comonomers yield mer units having the general formula:

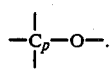

In accordance with certain preferred aspects of the present invention, the cyano-containing monomer is either 3-cyanomethyl-3-methyl oxetane (CYMMO), wherein $R^3$ is cyanomethyl and $R^4$ is methyl and 3,3-Bis(cyanomethyl)oxetane (BCYMO), wherein $R^3$ and $R^4$ are each cyanomethyl. In the case of each of CYMMO and BCYMO, $R^1$, $R^2$, $R^5$ and $R^6$ are each hydrogen. The CYMMO monomer is a novel compound, the synthesis of which is described in Example 1, hereinbelow. The BCYMO monomer was described by P. Cornard and F. Govaert, *Mededel. Vlaam. Chem. Ver.* 16, 8+ (1954); *Chem. Abstr.* 50, 4108i (1956). Herein, homopolymers of both CYMMO and BCYMO mer units are produced, as are copolymers of CYMMO and BCYMO. In addition, CYMMO, BCYMO and CYMMO/BCYMO mixtures have been copolymerized with tetrahydrofuran (THF). As a comonomer, THF has advantages in that it affords the binder that is formed with good structural properties; and also, it does not detract significantly from the energy of the polymer. However, a homopolymer of THF, in itself, is not miscible with nitrate esters.

Polyethers are formed from the cyclic ether monomers by cationic polymerization. Generally, an initator mixture is formed from an adduct of a substance, such as a diol, e.g., 1,4-butane diol, and a catalyst for cationic polymerization, e.g., $BF_3$-etherate. A number of suitable organic compounds and catalysts which may be used to form initiator adducts for cyclic ether polymerization are described in U.S. Pat. No. 4,393,199, the teachings of which are incorporated herein by reference. The initiator mixture reacts with one of the available monomers to form an initiating species; then polymerization proceeds by chain elongation until the supply of available monomers is substantially, e.g., over 85%, exhausted.

The length of the polyethers is generally a function of initiator concentration relative to available monomers with the average length of the chain being approximately the number of available monomer molecules divided by the number of initiator adducts. Generally, polyethers used in binders are tailored to have number average molecular weights (Mn) of from about 1,000 to about 10,000 although lower or higher molecular weight polyethers may be preferred for certain purposes. Polydispersity of polyethers formed in accordance with the present invention range from about 1.5 to about 2.5. Generally, the molar ratio of mer units in the polyether which is formed reflects the molar ratios of available monomers; however, in some cases, there may be considerable divergence, particularly if one of the monomeric species is considerably less reactive in the polymerization reaction.

The polymerization reaction may be performed in a suitable solvent, such as methylene chloride. Alternatively, if one of the monomers, e.g., THF, serves as a solvent, the polymerization may be carried out in the absence of additional solvent.

Gumstocks or binder materials are formed from the polyethers by curing with isocyanates having a functionality of at least two, e.g., toluene diisocyanate. To promote chain elongation, at least one equivalent of isocyanate (NCO) is required; however, an NCO-to-OH ratio of about 1.3 or above is preferably used where some of the NCO may be expected to be consumed by reaction with other available species, e.g., in propellant formulations. Preferably, cross-linking is also promoted, for example, by using an isocyanate of higher functionality and/or by adding a separate cross-linking agent, such as trimethylolethane. A cross-linked density of at least about 10% is generally preferred. When propellant or explosive grains are produced, curing is effected in the presence of the solids and the plasticizer, whereupon the solids and plasticizer are dispersed and immobilized throughout the cured binder. Temperatures in the range of 100° F. (38° C.) to about 150° F. (66° C.) promote an acceptable curing rate. A cure catalyst, such as a heavy metal derivative, may be added to promote rapid curing.

Herein, nitrate ester compatibility refers to miscibility (solubility) with materials commonly used as plasticizers in propellant binders. These include, but are not limited to nitroglycerin (NG); mono, di and triethyleneglycol dinitrate; butanetriol trinitrate (BTTN), trimethylolethane trinitrate (TMETN) and mixtures thereof.

The invention herein is intended to encompass plasticized binders useful in high-energy compositions, such as a propellant. Plasticized binders comprise a nitrate ester plasticizer plus an isocyanate-cured polyether as described above, the wt. ratio of plasticizer to cured binder is at least about 2:1 and preferably at least about 2.5:1.

The invention herein is further intended to encompass high-energy compositions, such as propellant compositions. The propellant compositions comprise between about 70 and about 85 percent particulate solids, including fuel material particulates and oxidizer particulates and the balance substantially all nitroester plasticized binder having a plasticizer-to-cured binder weight ratio of at least about 2:1 and preferably at least about 2.5:1. A typical particulate fuel material is aluminum. Particulate oxidizer materials include but are not limited to ammonium perchlorate (AP), cyclotetramethylene tetranitramine (HMX), cyclotrimethylene trinitramine (RDX), and mixtures thereof.

The invention will now be described in greater detail by way of specific examples.

Example 1

3-Cyanomethyl-3-methyloxetane (CYMMO)

In a three-necked, 2-liter flask equipped with a mechanical stirrer, reflux condenser, and drying tube were combined 3-chloromethyl-3-methyloxetane (261 g, 2.2M), sodium cyanide (160 g, 3.25M), and 1.1 liter ethanol. The stirred mixture was refluxed for 60 hr. The reaction was cooled and filtered, and the filter cake was washed with a minimum amount of diethyl ether. The combined organic fractions were reduced in vacuum and the remainder was distilled to give 180 g (74%) of CYMMO as a clear liquid, bp 74°-76° C./5 Torr. Elemental Analysis: Theory—C 64.86%, H 8.11%, N 12.61%; Found—C 64.88%, H 8.30%, N 12.6%.

Example 2

General Polymerization Procedure

An appropriately sized resin flask, equipped with addition funnel, mechanical stirrer, and gas inlet is dried in an oven and cooled under a blanket of inert gas. The flask is charged with THF, followed by 1,4-butanediol. The reactor is then cooled to the desired temperature (typically $-10°$ C.) and boron trifluoride-etherate is added. After 15 minutes, dropwise addition of the oxetane monomer is started. When the oxetane addition is complete, the stirring is continued at $-10°$ C. for 48 to 72 hr.

The reaction is then quenched by addition of saturated aqueous sodium bicarbonate. Enough methylene chloride is added to facilitate separation of the layers. The organic fraction is separated, washed a second time with saturated aqueous bicarbonate, and then washed with brine. The organic fraction is dried over magnesium sulfate, and the majority of the solvent is removed using a rotary evaporator. The remainder of the monomer and solvent is removed by heating to 45° C. at less than 1 Torr. overnight. For efficient removal of low molecular weight materials, it is necessary that the sample be stirred during this drying process.

In every case, the stoichiometry of the reaction is one equivalent of butanediol to two equivalents of boron trifluoride-etherate. The theoretical molecular weight of the product polymer is determined by the molar ratio of 1,4-butanediol to total monomer.

Example 3

A copolymer was prepared from a 70/30 mixture of THF/CYMMO. The 70/30 THF/CYMMO copolymer was a viscous liquid at room temperature and was fully miscible with 1:1 TMETN at 4° C. Satisfactory gumstocks were obtained when the copolymer was cured with Desmodur ® N-100 with 1:1 TMETN as plasticizer.

Example 4

To further improve the low-temperature properties, two additional batches of THF/CYMMO polymer were prepared using a lower portion of CYMMO monomer in the synthesis, i.e., 80/20 and 90/10 THF/CYMMO mixture. Both polymers were found to be viscous oils which flow at room temperature, unlike the 70/30 THF/CYMMO polymer reported above. The 80/20 THF/CYMMO polymer was noted as being completely miscible with nitrate esters at room temperature, but the mixture became very slightly clouded at 3° C. Both polymers had a functionality near 2 and a lower $T_g$ than the 70/30 polymer. The polydispersity of both was improved over the 70/30 THF/CYMMO polymer; however, the yield was reduced.

Example 5

A 300 g sample of 80/20 (starting) THF/CYMMO was prepared for characterization. Analysis of the product showed that it consists of 75 percent tetrahydrofuran-derived material and 25 percent oxetane-derived material. By gel permeation chromatography (GPC) analysis, the sample had an Mn of 5500 and an Mw of 8300, with a polydispersity of 1.5. The hydroxy equivalent weight by acetylation was 2500. The sample was miscible with TMETN and was successfully cured in the presence of 50 percent TMETN as plasticizer.

Example 6

A 58/42 THF/CYMMO mixture was polymerized with a target molecular weight of 2500. These values were chosen in view of experience with the system as those likely to produce a 50/50 polymer with an Mn of 3000. The actual product, as determined by gel permeation chromatography, had an Mn of 4080, and Mw of 6730, and a composition of 48/52 THF/CYMMO as determined by nuclear magnetic resonance spectroscopy. This polymer was miscible at 2.5:1 with TMETN at 4° C.

Example 7

THF/CYMMO copolymers with target molecular weights near 2,000 to 3,000 were prepared. The actual properties of the polymers are given in Table 1 below.

TABLE 1

| Preparation of Low $M_n$ 50/50 THF/CYMMO Copolymers | | | | |
|---|---|---|---|---|
| Stoich Mw | Observed Mn | Observed Mw | Q | THF/CYMMO |
| 2500 | 4070 | 6680 | 1.6 | 48/52 |
| 2000 | 3030 | 5135 | 1.7 | 51/49 |
| 1500 | 3080 | 5770 | 1.9 | 55/45 |

Example 8

THF/CYMMO copolymers were cured as gumstocks with Desmodur ® N-100 isocyanate at an NCO-/OH ratio of 1.5:1, using either triphenyl bismuth (TPB) or dibutyltin dilaurate (DBTDL) as the catalyst with TPB giving generally a harder cure. Shore A hardness measurements were between 40 and 63. Cured plasticized gumstocks were prepared with a 3:1 NG/TMETN system. Preliminary propellant formulations of the 80/20 low molecular weight THF/CYMMO showed good casting properties and curability. Initial burning rate measurements indicated no deviation from the baseline PCP propellant.

Example 9

Propellant was formulated with the THF/CYMMO prepolymers and several plasticizer systems. Mechanical property trends for propellant systems using THF/CYMMO copolymers are indicated in Tables 2 and 3 below.

TABLE 2

| Tactical Propellant Properties[a] | |
|---|---|
| Property | |
| $E^{2.7}$ kPa (psi) (77° F.) | 1137 (165) |
| $\sigma_m/\sigma_m^c$ k Pa (psi) (77° F.) | 193/434 (28/63) |
| $\epsilon_m/\epsilon_f$ % (77° F.) | 116/126 |
| $\epsilon_m^c$ % (77° F.) | 124 |
| $\epsilon_m/\epsilon_f$ % ($-65°$ F.) | 728 |
| $\epsilon_m^c$ % ($-65°$ F.) | 7 |
| Shore A | 20 |
| EOMV kp | 59.4 |

[a]Propellant formulated with 70/30 THF/CYMMO; TMETN plasticizer; NCO/OH = 1.3; Pl/Po = 2.5; 79% total solids.

TABLE 3

| | Tactical Propellant Properties[a] | |
|---|---|---|
| | Mix Number | |
| Property | 4-4 | 4-3 (Control) |
| $E^{2.7}$ kPa (psi) (77° F.) | 1516 (220) | 5870 (852) |
| $\sigma_m/\sigma_m^c$ k Pa (psi) (77° F.) | 234/317 (34/46) | 579/689 (84/100) |

TABLE 3-continued

| | Tactical Propellant Properties[a] | |
|---|---|---|
| | Mix Number | |
| Property | 4-4 | 4-3 (Control) |
| $\epsilon_m/\epsilon_f$ % (77° F.) | 30/36 | 19/30 |
| $\epsilon_m^c$ % (77° F.) | 30 | 19 |
| $\epsilon_m/\epsilon_f$ % (−65° F.) | 5/186 | 10/19 |
| $\epsilon_m^c$ % (−65° F.) | 120 | 10 |
| Shore A | 30 | 49 |
| EOMV kp | 41 | 57 |

[a]Propellants made by slurry mixing.
[b]4-4 80/20 THF/CYMMO prepolymer; Pl/Po = 2.5; NG/TMETN = 3.0; NCO-/OH = 1.5. 4-3 PCP 0260/Thanol binder; Pl/Po = 2.5; NG/TMETN = 3.0; NCO/OH 1.3.

While the invention has been described in terms of certain preferred embodiments, modifications obvious to one with ordinary skill in the art may be made without departing from the scope of the present invention.

Various features of the invention are set forth in the following claims.

What is claimed:

1. A propellant composition comprising between about 70 and about 85% solids, including fuel material particulates and oxidizer particulates, balance substantially a nitroester plasticizer and a binder, said binder comprising (1) a polyether having a functionality of about 2 or greater and having between about 20 and 100 molar percent mer units of the formula:

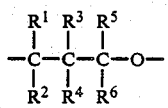

wherein at least four of $R^1$–$R^6$ are —H; one or two of $R^1$–$R^6$ is —$(CH_2)_n$—CN, wherein n is at least 1, and any remaining one of $R^1$–$R^6$ is an alkyl group, balance mer units being residues of compounds selected from the group consisting of ethylene oxide, other oxetanes, tetrahydrofuran, substituted tetrahydrofuran, and mixtures thereof.

2. A composition in accordance with claim 1 wherein said balance mer units consist essentially of residues of tetrahydrofuran.

3. A composition according to claim 1 wherein $R^3$ is —$CH_3$ and $R^4$ is —$CH_2$—CN.

4. A composition in accordance with claim 3 wherein said balance mer units consist essentially of residues of tetrahydrofuran.

5. A composition according to claim 1 wherein $R^3$ and $R^4$ are each —$CH_2$—CN.

6. A composition in accordance with claim 5 wherein said balance mer units consist essentially of residues of tetrahydrofuran.

7. A composition according to claim 1 wherein the weight ratio of plasticizer to binder is a least about 2:1.

8. A composition according to claim 1 wherein said plasticizer is selected from the group comprising nitroglycerin: mono-, di-, and triethyleneglycerol trinitrate, butanetriol trinitrate, trimethylolethane trinitrate, and mixtures thereof.

* * * * *